(12) United States Patent
Cambronne et al.

(10) Patent No.: US 8,192,451 B2
(45) Date of Patent: Jun. 5, 2012

(54) CUTTING AND CORING ATHERECTOMY DEVICE AND METHOD

(75) Inventors: Matthew D. Cambronne, Moundsview, MN (US); Robert E. Kohler, Lake Elmo, MN (US); Stephen Latham, Sun Prairie, WI (US); Jesse C. Darley, Madison, WI (US)

(73) Assignee: Cardiovascular Systems, Inc., St. Paul, MN (US)

( * ) Notice: Subject to any disclaimer, the term of this patent is extended or adjusted under 35 U.S.C. 154(b) by 432 days.

(21) Appl. No.: 12/466,164

(22) Filed: May 14, 2009

(65) Prior Publication Data

US 2009/0306691 A1 Dec. 10, 2009

Related U.S. Application Data

(60) Provisional application No. 61/058,971, filed on Jun. 5, 2008.

(51) Int. Cl.
*A61B 17/22* (2006.01)

(52) U.S. Cl. .......................................... 606/159; 604/22

(58) Field of Classification Search .................. 606/159, 606/170; 604/22, 508
See application file for complete search history.

(56) References Cited

U.S. PATENT DOCUMENTS

| | | | |
|---|---|---|---|
| 4,273,128 A | 6/1981 | Lary | |
| 4,631,052 A | 12/1986 | Kensey | |
| 4,765,332 A | 8/1988 | Fischell et al. | |
| 4,886,061 A | 12/1989 | Fischell et al. | |
| 4,926,858 A | 5/1990 | Gifford, III et al. | |
| 5,069,679 A | 12/1991 | Taheri | |
| 5,100,425 A | 3/1992 | Fischell et al. | |
| 5,176,693 A | 1/1993 | Pannek, Jr. | |
| 5,192,291 A | 3/1993 | Pannek, Jr. | |
| 5,522,825 A | 6/1996 | Kropf et al. | |
| 5,772,674 A | 6/1998 | Nakhjavan | |
| 5,902,313 A | 5/1999 | Redha | |
| 5,910,150 A * | 6/1999 | Saadat | 606/159 |
| 5,941,869 A | 8/1999 | Patterson et al. | |
| 6,165,187 A | 12/2000 | Reger | |
| 6,468,227 B2 | 10/2002 | Zimmon | |
| 6,540,722 B1 | 4/2003 | Boyle et al. | |
| 6,652,548 B2 * | 11/2003 | Evans et al. | 606/159 |
| 6,685,718 B1 | 2/2004 | Wyzgala et al. | |
| 6,695,813 B1 | 2/2004 | Boyle et al. | |
| 6,702,834 B1 | 3/2004 | Boylan et al. | |
| 6,730,104 B1 | 5/2004 | Sepetka et al. | |
| 7,217,255 B2 | 5/2007 | Boyle et al. | |
| 7,252,674 B2 | 8/2007 | Wyzgala et al. | |
| 2002/0010487 A1 | 1/2002 | Evans et al. | |

(Continued)

FOREIGN PATENT DOCUMENTS

WO WO 01/76458 10/2001

(Continued)

*Primary Examiner* — Victor Nguyen
(74) *Attorney, Agent, or Firm* — Winthrop & Weinstine, P.A.

(57) ABSTRACT

The invention provides a rotational and/or axially translatable atherectomy system, device and method having a flexible, elongated drive shaft or catheter having an expandable and collapsible conical coil with a cutting edge on the coil's large diameter proximal end. When retracted, the coil's sections are collapsed around each other, held together in the retracted position by a sheath that, when distally retracted, allows the coil to automatically expand. The coil is expanded at a point distal to the occlusion, then pulled proximally to cut the occluding material near the lumen wall. The proximal pulling force may be combined with low-speed rotation and/or translation and/or axial vibration at low to ultrasonic frequency.

16 Claims, 1 Drawing Sheet

U.S. PATENT DOCUMENTS

| | | |
|---|---|---|
| 2003/0055480 A1 | 3/2003 | Fischell et al. |
| 2004/0006358 A1 | 1/2004 | Wulfman et al. |
| 2005/0216030 A1 | 9/2005 | Sepetka et al. |
| 2006/0116702 A1 | 6/2006 | Goto et al. |
| 2007/0179513 A1 | 8/2007 | Deutsch |
| 2008/0039881 A1 | 2/2008 | Greenberg |

FOREIGN PATENT DOCUMENTS

| | | |
|---|---|---|
| WO | WO 03/088809 | 10/2003 |
| WO | WO2008/021886 | 2/2008 |

\* cited by examiner

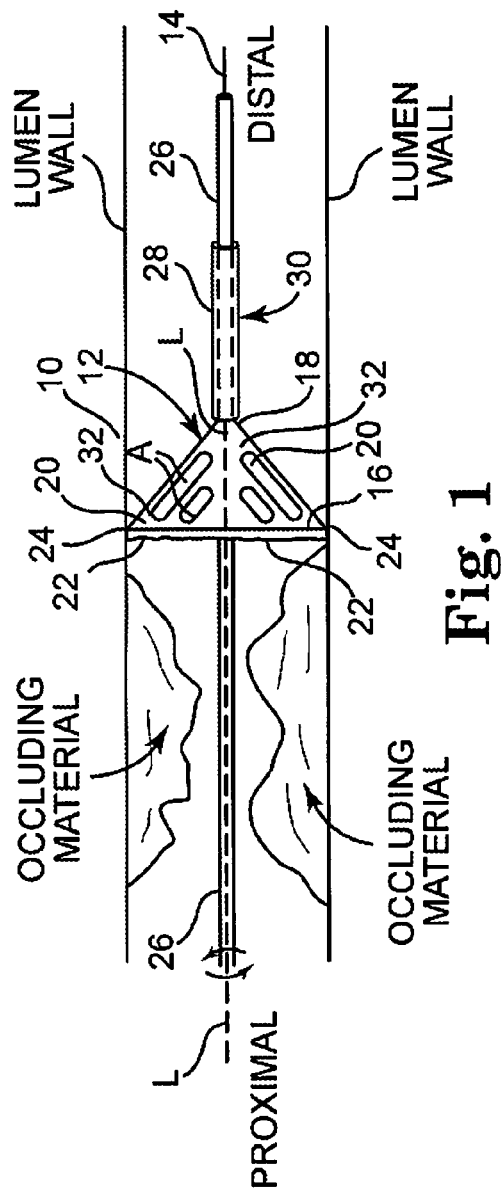
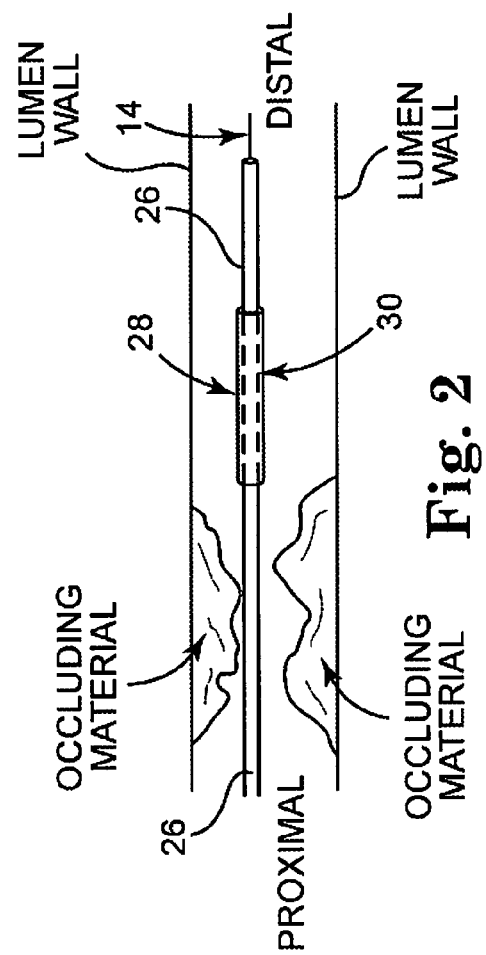

CUTTING AND CORING ATHERECTOMY DEVICE AND METHOD

CROSS-REFERENCE TO RELATED APPLICATIONS

The present application claims priority to provisional application No. 61/058,971, filed on Jun. 5, 2008 under the title, "LARGE VESSEL CORING ATHERECTOMY DEVICE", the contents of which are incorporated by reference herein.

BACKGROUND OF THE INVENTION

1. Field of the Invention

The invention relates to devices and methods for removing tissue from body passageways, such as removal of atherosclerotic plaque from arteries, utilizing a rotational atherectomy device.

2. Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patentcy of the opened artery. For non-calcified lesions, balloon angioplasty most often is used alone to open the artery, and stents often are placed to maintain patentcy of the opened artery. Studies have shown, however, that a significant percentage of patients who have undergone balloon angioplasty and had a stent placed in an artery experience stent restenosis—i.e., blockage of the stent which most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patentcy of the artery.

Several kinds of rotational atherectomy devices have been developed for attempting to remove stenotic material. In one type of device, such as that shown in U.S. Pat. No. 4,990,134 (Auth), a concentrically shaped ellipsoidal burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently, since the burr is of a fixed resting diameter, more than one size burr must be utilized to open an artery to the desired diameter.

U.S. Pat. No. 5,681,336 (Clement) provides an eccentric tissue removing burr with a coating of abrasive particles secured to a portion of its outer surface by a suitable binding material. This construction is limited, however because, as Clement explains at Col. 3, lines 53-55, that the asymmetrical burr is rotated at "lower speeds than are used with high speed ablation devices, to compensate for heat or imbalance." That is, given both the size and mass of the solid burr, it is infeasible to rotate the burr at the high speeds used during atherectomy procedures, i.e., rotational speeds within the range of about 20,000-200,000 rpm. Essentially, the center of mass offset from the rotational axis of the drive shaft would result in development of significant and undesirable centrifugal force, exerting too much pressure on the wall of the artery and creating too much heat and excessively large particles. As with Auth, the burr size is fixed and may require using more than one size burr to open the subject lumen to the desired diameter.

U.S. Pat. No. 6,132,444 (Shturman) and U.S. Pat. No. 6,494,890 (Shturman) both commonly assigned, disclose, inter alia, an atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. The orbital rotational motion is primarily due to the offset of the center of mass of the enlarged eccentric section from the drive shaft's rotational axis. Since the enlarged eccentric section may comprise drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. The disclosure of U.S. Pat. Nos. 6,132,444 and 6,494,890 are each hereby incorporated by reference in their entirety.

Each of the above solutions initiate ablation at some access point roughly near the center of the lumen and may require creating a pilot hole to allow the ablating element entry into the access point sufficient to initiate cutting and/or grinding the occluding material. In addition, high-speed rotation is used to generate the ablating forces of the foregoing solutions, thereby potentially generating heat and trauma to healthy tissue. Moreover, these devices do not automatically expand to match the changing diameter of the vessel wall while atraumatically coring and cutting away unhealthy tissue as the atherectomy procedure proceeds.

Thus, it would be highly advantageous to provide an atherectomy system, device and method that initiates cutting of occluding material at a point near the vessel wall, in atraumatic fashion, using low-speed rotation and/or translational and/or axial vibration while the ablating element is pulled proximally along the vessel wall to cut and core the occluding material away from the wall.

The present invention addresses, inter alia, these needs.

BRIEF SUMMARY OF THE INVENTION

The invention provides a rotational atherectomy system, device and method comprising a flexible, elongated drive shaft or catheter comprising an expandable and collapsible conical coil with a cutting edge on the coil's large diameter proximal end. When retracted, the coil's sections are collapsed around each other, held together in the retracted position by a sheath that, when distally retracted, allows the coil to automatically expand. The coil is expanded at a point distal to the occlusion, then pulled proximally to cut the occluding material near the lumen wall. The proximal pulling force may be combined with low-speed rotation and/or translation and/or axial vibration at low to ultrasonic frequency.

An object of the invention is to provide a rotational atherectomy device with a cutting and coring expanded cutting diameter that is larger than its retracted diameter.

Another object of the invention is to provide a rotational atherectomy device having a plurality of expanded cutting diameters that naturally meet and biasingly oppose lumen walls with diameters of up to 9 mm.

Another object of the invention is to provide a rotational atherectomy device comprising expanding the device distal to the occluding material and pulling proximally to achieve cutting and coring of occluding material.

Another object of the invention is to provide a rotational atherectomy device comprising expanding the device proximal to the occluding material and pushing distally to achieve grinding a hole through the occluding material.

Another object of the invention is to provide a rotational atherectomy device comprising rotation to achieve grinding and/or cutting and coring of occluding material.

Another object of the invention is to provide a rotational atherectomy device comprising vibration to achieve grinding and/or cutting and coring of occluding material.

Another object of the invention is to provide a rotational atherectomy device comprising ultrasonics to achieve grinding and/or cutting and coring of occluding material.

Another object of the invention is to provide a system and methods to achieve, inter alia, the above objectives.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

FIG. 1 is a side view of one embodiment of the present invention.

FIG. 2 is a side view of one embodiment of the present invention.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Generally the present invention comprises a cutting atherectomy device for coring a passage through body lumen, e.g., an artery that is otherwise at least partially occluded. The invention comprises a first retracted position for delivery through the patient's vasculature to the occlusion, and a second expanded position for cutting and coring. The cutting element comprises a blade in the form of a collapsible conical coil that is retractable, i.e., collapsible, from the expanded position and expandable from the retracted position. The cutting blade or edge is located on the larger diameter portion of the cutting element and is oriented so that the cutting blade or edge is facing proximally and the smaller diameter portion of the cutting element is oriented distal to the cutting blade. Thus, the interior surface of the expanded conical coil cutting element is also facing proximally.

The cutting element comprises an expanded diameter of up to 9 mm when fully deployed and expanded and is further unrestricted by lumen diameters less than 9 mm. As a consequence, the cutting element expands automatically to the diameter of any lumen since the cutting element expands naturally and automatically to provide biasing oppositional force against the lumen wall and is able to dynamically adapt to changing lumen diameters. An outer ring may be provided around the largest diameter portion of the cutting element to ensure that the cutting blade does not damage healthy tissue. In addition, the cutting blade may be angled slightly toward the longitudinal axis of the cutting element to move the cutting blade further still away from the healthy lumen wall tissue.

The cutting element is preferably initially located distally to the occlusion by delivery through the occlusion in the retracted position in preparation for the atherectomy procedure. When positioned, the cutting element is expanded and pulled proximally for cutting and coring the occluding material away from the lumen wall. The cutting effects provided by the proximal pulling force and the cutting blade may be aided and supplemented by a low-speed rotation supplied by the operator and/or by automated and/or motorized means. Further, vibration and/or pulsation may aid the cutting blade's efficacy via a piezo transducer and/or ultrasonic generator(s).

Turning now to the Figures, the present invention will be examined in detail.

FIG. 1 illustrates the present invention 10 with cutting element 12 in an expanded position over pre-positioned guide wire 14, with the large diameter section 16 located proximally relative to the small diameter section 18 of the cutting element 12. Therefore, the inner surface of the conical cutting element 12 is illustrated as facing in a proximal direction, in the embodiment shown the cutting element 12 is in an expanded position distal to the occluding material.

The cutting element 12 may comprise more than one flexible coil section 20, the more than one coil section 20 being collapsible to achieve the retracted position of FIG. 2 and expandable to achieve the expanded position of FIG. 1. Such an arrangement is well known, e.g., in food strainers and the like, wherein the more than one section slides over the adjacent sections to expand and collapse the device. The present cutting element 12 is thereby capable of winding tightly to a small diameter around the flexible shaft in the retracted position and unwinding and expanding to achieve an expanded position. The expanded position comprises a range of possible expansions having a dynamically adaptable and fluid range of diameters for the large diameter section 16. This range of large diameter section 16 diameters results from the accommodating and dynamic adaptability of the cutting element 12. The more than one coil section 20 of the cutting element 12 is urged to unwind when actuated, thereby automatically expanding to press against the sides of the lumen wall at the point of the lumen wall's smallest diameter if the lumen wall is not perfectly circular. This automatic expansion may be driven by a number of mechanisms, including but not limited to a clock spring attached to each of the more than one coil sections 20, biasing the more than one coil section 20 to the maximum expanded position which exceeds 9 mm. When the expanded position is less than the maximum expanded position, a biasing force is exerted by the large diameter section 16 on the lumen wall at the points that the cutting element 12 is in contact with lumen wall. As the atherectomy procedure proceeds and/or the cutting element 12 is moved proximally and distally, the lumen wall diameter may change with a concomitant, automatic and accommodating change in expanded position diameter of the cutting element's large diameter section 16.

Each of the cutting sections 20 comprises a cutting blade 22 attached to the upper surface 24 of cutting section 20. Therefore, the cutting blades 22 expand and retract in concert with the associated coil section 20.

One or more of the coil sections 20 may comprise one or more apertures A therethrough, to allow perfusion as well as allowing debris to flow through to a distal debris capture device (not shown) as is well known in the art.

The cutting element 12 is attached to a flexible rotatable and axially translatable shaft 26. The flexible shaft 26 may comprise a lumen therethrough (not shown) to allow fluid communication therethrough as is well known in the art. A sheath 28 comprising a lumen 30 therethrough may be moved proximally and distally over flexible shaft 26 by, e.g., an actuation wire as is well known in the art and not shown in the figures. For example, sheath actuator wire may be in operative attachment to the sheath 28 and extend through flexible shaft lumen to the operator who may pull the sheath wire proximally to move the sheath 28 proximally and/or push the sheath wire distally to move the sheath 28 distally over the flexible shaft 26 and/or cutting element 12. Near the distal end of the flexible shaft 26, the cutting element 12 is fixedly attached. The sheath lumen 30 comprises an inner diameter that is larger than the outer diameter of the retracted cutting element 12 to allow retraction therein. The sheath 28 is, in FIG. 1, illustrated in a deployed position, distal to the cutting element 12, whereby cutting element 12 is in an expanded position.

The flexible shaft 26 may comprise a flexible wire coil or a slotted tube in various embodiments. If the flexible shaft 26 comprises flexible wire coil, it may be composed of stainless steed that is in a spring temper or higher tensile condition. Examples of stainless steel that may be used in the present invention's flexible shaft 26 comprise MP35N, 35NLT, L605 or FWM 1058 and the like. If the flexible shaft 26 comprises a slotted tube, it may comprise Nitinol or some other shape memory metal or material having high elasticity. The slots in the slotted flexible tube 26 embodiment may be laser or mechanically cut into the tube wall to give it flexibility and kink resistance.

Turning now to FIG. 2, one embodiment of the present invention is illustrated in the retracted position. Thus, the sheath 28 is drawn proximally over the expanded cutting element 12 of FIG. 1 by, e.g., the operator pulling the sheath actuating wire proximally causing the sheath 28 to move in a proximal direction as discussed above. The sheath 28 is capable, upon application of sufficient proximal force, sliding proximally over the cutting element 12, reducing its expanded position to a fully retracted position within the sheath's lumen 30. To achieve this retraction, the sheath 28 must be pulled proximally with sufficient force to overcome the outwardly biased force of the cutting element 12 and cause the cutting element 12 and its coil sections 20 to collapse and wind around the flexible shaft 26 and within the sheath's lumen 30.

Various embodiments of the present invention comprise features and elements that facilitate an atraumatic atherectomy procedure by ensuring that the cutting blades 22 do not contact the healthy tissue of the lumen wall as cutting and coring of the occluding material proceeds. As discussed above, the cutting blades 22 are preferably located on the large diameter portion 16 of the expanded cutting element 12. In certain embodiments, the cutting blades 22 may be offset inwardly away from the outermost diameter of the conical cutting element's large diameter portion 16. This offset, when present, assists in keeping the cutting blades 24 away from the healthy tissue of the lumen wall.

Further, the cutting blades 24 are, preferably, arranged and oriented so that their cutting edges are substantially parallel with the cutting element's longitudinal axis L. However, in certain embodiments, the cutting blades 24 may comprise an orientation that creates an acute angle with respect to the edges of the blades 24 and the cutting element's longitudinal axis L. In other words, in these embodiments, the cutting blades 24 are tilted slightly and pointing slightly inwardly towards the longitudinal axis L. This acute angle may preferably be in the range of 89 degrees to 60 degrees, though the skilled artisan will recognize a larger range of acutely angling the cutting blades 24 relative to the longitudinal axis L may be efficacious; each such angle is within the scope of the present invention. This inward tilting of the cutting element's blade edges, when present, assists in moving the cutting surfaces of the cutting element 12 away from the healthy tissue of the lumen wall.

Moreover, in certain embodiments of the present invention, an outer ring (not shown) may be disposed around the outer diameter of the conical cutting element's large diameter portion 16, effectively moving the cutting blades 24 away from the healthy tissue of the lumen wall.

It will be clear to the skilled artisan that one or more of the above-described autramatic features, i.e., the outer ring, acutely angling the cutting blades 24, and offsetting the cutting blades 24 away from the outer large diameter 16 of the cutting element 12, may be used, whether alone or in any combination, to reduce trauma during cutting and coring.

In alternate embodiments of the present invention abrasive may be coated onto the outer surface 32 of the cutting element 12 so as to present an abrasive outer surface to occluding material if the expanded cutting element 12 is advanced distally through occluding material. This outer abrasive surface 32 may then be used expanded proximal to the occluding material and pushed therethrough, resulting in a grinding effect by either the proximal motion and/or rotation and/or vibration and/or ultrasonics during the proximal pushing motion through the occluding material. Such an arrangement and method may be advantageous, e.g., in order to create an opening through the occluding material to enable the expanded cutting element 12 to achieve its coring cutting effect when pulled against the occluding material proximally. By way of example, the abrasive material may be any suitable material, such as diamond powder, fused silica, titanium nitride, tungsten carbide, aluminum oxide, boron carbide, or other ceramic materials. The abrasive material may comprise diamond chips (or diamond dust particles) attached and/or coated directly to the outer surface 32 of the cutting element 12, such attachment may be achieved using well known techniques, such as conventional electroplating or fusion technologies (see, e.g., U.S. Pat. No. 4,018,576). Alternately the outer surface 32 of the cutting element 12 may comprise an external tissue removing surface which has been roughened to provide a suitable abrasive surface. In yet another variation, the outer surface 32 of the cutting element 12 may be etched or cut (e.g., with a laser) to provide small but sharp cutting surfaces.

As described above, the flexible shaft 26 is capable of rotating slowly to achieve the cutting and coring effect contemplated by the present invention 10. When this occurs, the cutting blades 24 cut the occluding material but not the healthy tissue of the lumen wall.

Still more alternatively, the flexible shaft 26 may rotate in two directions, thus comprising bi-directional rotation, and the cutting element 12 and cutting blades 24 may comprise a grinding element on one rotational side of the cutting blades 24 which grinds occluding material when the flexible shaft 26 and cutting element 12 is rotated in the direction wherein grinding element grindingly engages occluding material. Further, the cutting element 12 and cutting blades 24 may comprise a cutting surface on the rotational surface of the cutting blades 24 opposite that of the grinding element, wherein rotation of the flexible shaft 26 and cutting element 12 in the opposite direction results in the cutting surface engaging, and cutting, occluding material. In this manner, the cutting element 12 may comprise, in one rotational direction, a grinding or abrasive effect, and in the other rotational direction, a cutting effect.

In addition to rotational cutting when pulled proximally against the occluding material and/or grinding when pushed distally through the occluding material, the present invention may comprise a piezo transducer to initiate vibration which enhances the cutting and/or grinding of occluding material through vibrational energy. In this manner, the piezo transducer may induce vibratory motion resulting in cutting and coring of the occluding material. The vibratory motion may be induced axially and/or transversely. A resonant frequency may be employed to maximize this effect which may be used alone or in conjunction with proximal and/or distal pushing force, rotation and/or axial translation to achieve the cutting and coring of occluding material.

Further, the present invention may comprise an ultrasonic device which imparts high-frequency energy to the occluding material using an ultrasonic generator as is well known in the art to generate and/or produce ultrasonic energy. A transducer, e.g., a piezo transducer, may be used to transmit the ultrasonic energy received from the ultrasonic generator to the cutting element 12. The cutting element 12 may be induced to vibrate ultrasonically in either a transverse and/or axial (longitudinal) mode of vibration as is well known in the art. Such addition of ultrasonic energy results in tissue-destroying effects of the cutting element 12 that are not necessarily limited to the regions of the cutting element 12 and its blades that are in direct contact with the occluding material.

In a preferred embodiment of the present invention, the ultrasonic frequency employed should be ineffective toward tissues such as vascular tissues in the subject lumen wall. Thus, the range of effective, but atraumatic, frequencies will be within the range of about 20,000 Hertz to about 35,000 Hertz (20 kHz-35 kHz). Ultrasonic energy may be employed to maximize the cutting and/or coring of occluding material either alone or in conjunction with proximal and/or distal pushing force, rotation and/or axial translation.

The structure of the present invention having been described, we now turn to the operation of the present invention in its various embodiments.

A guide wire 14 is pre-positioned within the subject lumen and proximate the occluding material as is well known in the art. Preferably, the guide wire 14 will be extended through the occluding material and positioned distal to the occluding material. The flexible shaft 26, and cutting element 12 attached thereto, may then be positioned over the guide wire 14 and moved through the vasculature to a point proximate the occluding material. During insertion, the cutting element 12 is in a retracted position, held in retraction by sheath 28, within sheath's lumen 30.

If the retracted cutting element 12 cannot pass through the occluding material, it may be necessary to withdraw the device and create a pilot hole with another device. Alternatively, the cutting element 12 may be expanded at a point proximal to the occluding material so that the abrasive external surface 32 of the cutting element 12 may contact the occluding material upon distal translation of the cutting element 12 over the guide wire 14. Such axial translation, in combination with rotation in various embodiments, results in the abrasive material and/or abrasive outer surface 32 of the cutting element 12 to abrade the occluding material, thus allowing the cutting element 12 to create a pilot hole through it may pass whereupon the cutting and coring process may be initiated.

If, on the other hand, the retracted cutting element 12 can pass through the occluding material, it is preferred to translate the cutting element 12 distally through the occluding material. At this point, the sheath 28 is slid distally by the operator using, e.g., a sheath actuating wire. This results in the cutting element 12 automatically expanding to biasingly contact the lumen walls in response to the biasing force of the clock spring or equivalent.

The operator may then initiate proximal movement of the cutting element 12 by applying proximal force, either manually or by automated and/or motorized means that are in operative communication with the flexible shaft 26 and cutting element 12, to the flexible shaft 26 whereupon the cutting blades 24 come into contact with occluding material while avoiding the healthy lumen wall tissue. The proximal movement enables the cutting element 12 to translate axially into the occluding material. The cutting and coring is, in this manner, done around the outer circumference of the lumen wall, rather than from the middle of the lumen and working outwardly as with prior art devices.

The cutting and coring effect may be enhanced or optimized by reversing the rotational direction of the cutting element 12 and blades 24. Such bi-directional rotation may comprise a reciprocating rotational motion or may comprise a number of rotations in a first rotational direction, followed by a number of rotations in the opposite rotational direction. Such bi-directional rotation may further comprise a cutting effect in one rotational direction and a grinding effect in the opposing rotational direction.

The cutting and coring achieved by proximal force accompanied by rotation of the cutting element 12 and blades 24 may be further enhanced by reciprocating axial motion of the cutting element 12. Thus, the cutting element 12 may, as described above, be moved proximally and axially into the occluding material while the device is also rotating. The cutting element 12 may, either routinely or under certain circumstances to overcome difficult occlusions, then be axially translated slightly distally, then again translated proximally into the occlusion. Such reciprocating axial movement may be achieved by the operator manually and/or by automated or motorized means in operative communication and connection with the flexible drive shaft and cutting element as is well understood in the art.

In addition to the axial and rotational movements of the cutting element 12, vibration may be imparted to the cutting element 12 and cutting blades 24 to optimize grinding and/or cutting and coring of occluding material. Such vibrational optimization is provided, as discussed above, by a piezo transducer in operative communication with the flexible shaft and/or the cutting element 12 and cutting blades 24 to vibrate the cutting blades 24 against the occluding tissue. Such vibrational energy may comprise moving the cutting blades back and forth axially, transversely, i.e., side-to-side, and/or in an oscillatory trajectory.

Finally, grinding and/or cutting and coring may be further optimized by employing ultrasonic energy to assist the cutting blades 24 in their cutting and coring action as described above.

The debris created by the present invention passes through apertures in the coil section(s) of the cutting element 12 and is captured by a distal protection element as is well known in the art.

When the occlusion is cut, the operator may then actuate the sheath 28 via the sheath actuating wire, e.g., and slide the sheath 28 proximally toward the cutting element 12, engaging the smaller diameter portion 18 of cutting element 12, thus causing the expanded cutting element 12 to collapse and retract within the proximally sliding sheath's lumen 30. When fully retracted, the flexible shaft 26 and retracted cutting element may be withdrawn from the patient's vasculature.

Thus, a method of cutting and coring occluding material within a lumen using the present invention may comprise:

providing a flexible shaft having an outer diameter smaller than the inner diameter of the lumen;

providing a cutting element attached to the flexible shaft that is capable of expanded positions having diameters substantially equal to the inner diameter of the lumen and a retracted position having a diameter substantially less than the inner diameter of the lumen;

advancing the flexible shaft and retracted cutting element through the patient's vasculature to a point distal the occluding material;

actuating the cutting element to an expanded position;

proximally pulling the expanded cutting element to engage the occluding material;

rotating the expanded cutting element slowly to cut and core the occluding material in an atraumatic manner;

completing the cutting and coring;

actuating the expanded cutting element into the retracted position; and withdrawing the substantially straightened drive shaft from the lumen.

Alternate embodiments may comprise providing axial translation, reciprocating axial translation and/or rotation; bi-directional rotation with grinding effects in one rotational direction and cutting effects in the opposing rotational direction; enhancing the atraumatic cutting and coring by adding vibration and/or ultrasonic energy to the cutting element; providing apertures through the cutting element to allow cut debris to flow therethrough; and capturing debris in a distal protective device.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. An atherectomy device for grinding and/or cutting and coring occluding material within a lumen having at least one diameter, comprising:

a flexible elongated, rotatable shaft having an outer diameter less than the lumen and advanceable therethrough, the flexible shaft comprising a proximal end and a distal end, a cutting element attached proximate the distal end and capable of a retracted position having an outer diameter and a plurality of radially outwardly biased cone-shaped expanded positions having a plurality of outer diameters, each outer diameter matching the lumen's at least one diameter, the cutting element comprising a longitudinal axis, more than one coil section in expandable and retractable operative attachment, a large proximal diameter portion having an outer edge and a small distal diameter portion, cutting blades on the large proximal diameter portion, wherein the cutting blades face proximally and wherein the small distal diameter portion is located distal to the large proximal diameter portion and the cutting blades, and at least one aperture through the more than one coil section, wherein the retracted cutting element comprises an outer diameter, and a sheath slidably and operatively connected with the flexible shaft, the shaft having a lumen therethough, the shaft lumen having an inner diameter that is larger than the outer diameter of the retracted cutting element, the retracted cutting element held within the shaft lumen.

2. The atherectomy device of claim 1, the cutting blades forming an acute angle with the cutting element's longitudinal axis.

3. The atherectomy device of claim 1, further comprising an outer ring around the large proximal diameter portion of the cutting element.

4. The atherectomy device of claim 1, further comprising a piezo transducer in operative communication with the cutting element.

5. The atherectomy device of claim 4, further comprising an ultrasonic generator in operative communication with the piezo transducer.

6. The atherectomy device of claim 1, the cutting element further comprising an abrasive outer surface.

7. The atherectomy device of claim 1, further comprising a sheath actuator.

8. The atherectomy device of claim 1, further comprising the cutting blades being inwardly offset from the outer edge of the large diameter portion of the cutting element.

9. The atherectomy device of claim 1, further comprising a distal protective device to capture freed occluding material.

10. The atherectomy device of claim 1, further comprising an outer ring attached around the outer edge of the large proximal diameter portion of the cutting element.

11. The atherectomy device of claim 10, further comprising the cutting blades being inwardly offset from the outer edge of the large diameter portion of the cutting element.

12. The atherectomy device of claim 1, further comprising a piezo transducer in operative communication with the cutting element.

13. The atherectomy device of claim 12, further comprising an ultrasonic generator in operative communication with the piezo transducer.

14. The atherectomy device of claim 1, the cutting element further comprising an abrasive outer surface.

15. The atherectomy device of claim 1, further comprising a sheath actuator.

16. The atherectomy device of claim 1, further comprising a distal protective device to capture freed occluding material.

* * * * *